US006348599B1

United States Patent

(12) United States Patent
Cummins et al.
(10) Patent No.: US 6,348,599 B1
(45) Date of Patent: Feb. 19, 2002

(54) CYANINE DYES

(75) Inventors: William Cummins, Tring; Richard West, Uxbridge; John Anthony Smith, Rhiwbina, all of (GB)

(73) Assignee: Nycomed Amersham plc, Buckinghamshire (GB)

( * ) Notice: Subject to any disclaimer, the term of this patent is extended or adjusted under 35 U.S.C. 154(b) by 0 days.

(21) Appl. No.: 09/463,534

(22) PCT Filed: Jul. 27, 1998

(86) PCT No.: PCT/GB98/02232

§ 371 Date: Apr. 24, 2000

§ 102(e) Date: Apr. 24, 2000

(87) PCT Pub. No.: WO99/05221

PCT Pub. Date: Feb. 4, 1999

(30) Foreign Application Priority Data

Jul. 28, 1997 (GB) .......................................... 97305550

(51) Int. Cl.[7] ........................ C09B 23/02; C09B 23/10; C07D 209/02

(52) U.S. Cl. ....................................... 548/455; 548/462

(58) Field of Search ................................. 548/455, 462

(56) References Cited

FOREIGN PATENT DOCUMENTS

| | | |
|---|---|---|
| DE | 3912046 | * 3/1990 |
| EP | 0464543 | * 1/1992 |
| WO | 96-00902 | * 1/1996 |
| WO | 96-13552 | * 5/1996 |
| WO | 96-33406 | * 10/1996 |
| WO | 97-17076 | * 5/1997 |

OTHER PUBLICATIONS

Derwent Database WPI, Week 9729, Section Ch, Class B02 (1997).*

* cited by examiner

*Primary Examiner*—Floyd D. Higel
(74) *Attorney, Agent, or Firm*—Royal N. Ronning, Jr.

(57) ABSTRACT

A cyanine dye having the structure (1)

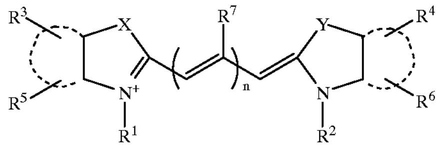

has an overall positive charge greater than +1, by virtue of the presence of one to five positively charged N or P or S atoms, and also has a reactive or functional group by which it may be linked to a biomolecule or a solid surface.

10 Claims, No Drawings

CYANINE DYES

The cyanine dye class has proved to be an extremely bright and versatile class of dyes in both photographic and biological applications. The addition of sulphonic acid and attachment of functionality for conjugation have allowed them to be fully exploited for biological research applications. The addition of sulphonic acids for additional water solubility and enhanced brightness has led to the dyes becoming overall neutral or negatively charged. As described in U.S. Pat. Nos. 5,268,486 and 5,486,616, the basic cyanine structure has a +1 overall positive charge e.g.

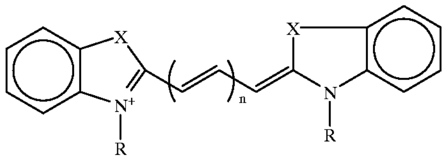

overall +1 charge

In certain applications dyes having several positively charged atoms can be of benefit. This invention addresses that need.

The invention provides a cyanine dye having the structure (1)

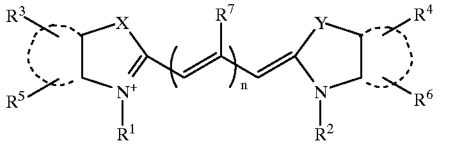

where the dotted lines represent the carbon atoms necessary for a one ring or a two or three fused ring system with 5 or 6 carbon atoms in each ring and $R^3$, $R^4$, $R^5$ and $R^6$ attached to the rings, X and Y. are independently elected from O, S and $CR^3_2$, where $R^8$ is $C_1$–$C_4$ alkyl, n is 1, 2 or 3, at least one of $R^1$, $R^2$, $R^3$, $R^4$, $R^5$, $R^6$ and $R^7$ comprises a reactive or a functional group, at least one of $R^1$, $R^2$, $R^3$, $R^4$, $R^5$, $R^6$ and $R^7$ incorporates one to to five positively charged nitrogen or phosphorus or sulphur atoms, any remaining $R^3$, $R^4$, $R^5$ and $R^6$ is independently selected from H, $SO^-_3$, Cl, Br, $OR^9$ and $SR^9$, where $R^9$ is $C_1$–$C_{10}$ alkyl or aryl or aralkyl, any remaining $R^1$ and $R^2$ is independently selected from $C_1$–$C_{10}$ alkyl or aryl or aralkyl either unsubstituted or substituted by $SO^-_3$, any remaining $R^7$ is selected from H and $C_1$–$C_{10}$ alkyl or aryl or aralkyl either unsubstituted or substituted by $SO^-_3$, provided that at least two positively charged atoms selected from nitrogen and phosphorus and sulphur are present in the groups $R^1$, $R^2$, $R^3$, $R^4$, $R^5$, $R^6$ and $R^7$, and provided that the first atom of $R^7$ (through which it is linked to the rest of the molecule) is H or C.

Preferably the cyanine dye has the structure (2)

(2)

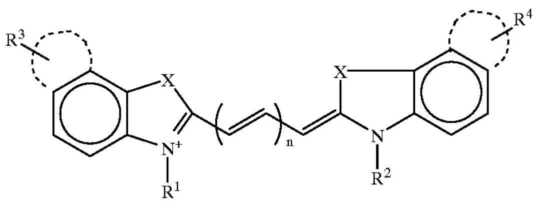

Preferably the cyanine dyes have an overall positive charge of +2 to +6. The overall charge of the dye may be considered as the number of positively charged nitrogen (or phosphorus or sulphur) atoms minus the number of sulphonate (or carboxyl or phosphate) groups. Thus for example, a dye having 3 positively charged nitrogen atoms and 0 or 2 or 4 sulphonate groups would have an overall charge of +3 or +1 or −1, respectively. The extent to which an atom or group is charged may depend on the pH of its environment.

Preferably a reactive or functional group is present as a structure -L-Q where L is a linker and Q is the reactive or a functional group. A reactive group of the dye can react with a functional group of a target molecule; or a functional group of the dye can react with a reactive group of a target molecule; whereby the target molecule becomes labelled by the dye. Preferably Q is a functional group selected from primary amine, secondary amine, hydrazine derivatives, hydroxylamine derivatives, and pyrazolone. Alternatively a functional group may be selected from sulphydryl, carboxyl, hydroxyl, thiophosphate, imidazole and carbonyl including aldehyde and ketone.

Preferably a reactive group is selected from succinimidyl ester, isothiocyanate, dichlorotriazine, isocyanate, haloacetamide, maleimide, sulphonyl halide, acid halide, alkylimido ester, arylimido ester, carbodiimide, phosphoramidite, anhydride and acyl azide.

By virtue of these functional and reactive groups, the cyanine dyes of the present invention are combined with target materials to form conjugates. Suitable target materials may include antibodies, antigens, proteins, carbohydrates, lipids, nucleotides, nucleic acids, polymer particles or glass beads. Thus for example, cyanine dyes having the preferred functional groups mentioned above are suitable for reacting with carbohydrates to form conjugates therewith.

L is a linker, which may contain 1–60 chain atoms selected from C, N, O, S and P, e.g. a straight chain of 1–30 carbon atoms in which are incorporated one or more N, O, S or P atoms. For example the linker may be $-(CH_2)_x-$ $-((CH_2)_p-O-(CH_2)_q)_y-$ $-((CH_2)_p-CONH-(CH_2)_q)_y-$ $-((CH_2)_p-Ar-(CH_2)_q)_y-$ where x is 1–30, preferably 1–10, p is 1–5, q is 0–5 and y is 1–5.

Present in the cyanine dye of the invention is a branched or straight chain incorporating 1–5 positively charged nitrogen or phosphorus or sulphur atoms. (Some or all of these positively charged N or P or S atoms may be present in the linker group L.). Preferably each positively charged atom is a nitrogen atom provided by a quatemary ammonium group, or alternatively by a protonated tertiary amino group, a guanidinium group, an imidazole group or a pyridinium group. Positively charged P and S atoms may be provided by phosphonium ions and sulphonium ions respectively. Preferably a branched or straight chain incorporating one to five positively charged nitrogen atoms is up to 60 chain carbon atoms and has the structure $—(CH_2)_mN^+R^{10}R^{10}R^{11}$ or $—CH_2—Ph—N^+R^{10}R^{10}R^{11}$ where m is 1 to 4, $R^{10}$ is $C_1–C_{10}$ alkyl, and $R^{11}$ is $C_1–C_{10}$ alkyl or $—(CH_2)_mN^+R^{10}R^{10}R^{11}$.

Or the linker group L and/or the chain incorporating positively charged nitrogen atoms may comprise one or more natural or artificial amino acid residues. It is a simple matter to introduce any number e.g. 1–20 of lysine residues, and if desired to quaternise the amino groups. Such linkers may contain the grouping $—(CO.NHW)_1—$ where r is preferably 1 to 6 and W is aminoalkyl or quaternised aminoalkyl such as $—(CH_2)_4NH_2$ or $—(CH_2)_4N^+R_3^{10}$ where $R^{10}$ is $C_1–C_{10}$ alkyl.

At least two positively charged nitrogen or phosphorus or sulphur atoms and preferably at least one reactive or functional group are present in pendant groups attached to the core structure of the dye. They may be positioned on the same group or different groups $R^1$, $R^2$, $R^3$, $R^4$, $R^5$, $R^6$ and $R^7$.

Preferably the cyanine dye has the structure (2)

wherein X and Y are $C(CH_3)_2$, n is 1 or 2, $R^1$ is $—(CH_2)_5—COOH$, $R^2$ is $—(CH_2)_3—N^+(CH_3)_2—(CH_2)_3—N^+(CH_3)_2(C_2H_5)$, and $R^3$ and $R^4$ are H.

The dyes described in the experimental section below have quaternary ammonium ions attached for the specific purpose of increasing the overall positive charge of the dye. The dyes have been made as carboxylic acids to enable their use in labelling DNA or other biological molecules via active ester derivatives. The increased positive charge may be beneficial in electrostatic interactions with DNA in certain specific applications and in providing labelled nucleotides having particular charges for other purposes. It is also envisaged that at least one sulphonic acid group can be added to any of the +3 (or more) dyes to give a dye that may have an overall positive or negative charge or may be neutral and may have improved photostability and brightness. This improvement is useful in applications such as difference gel electrophoresis technology as described in WO 96/33406 where the overall charge on the dye is of importance.

The carboxylic acid derivative can be reacted: either with diamine species such as 1,3-diaminopropane or ethylene diamine to provide a primary amine functional group; or with a protected hydrazine to generate a corresponding hydrazide which can be deprotected; e.g. for linking to carbohydrates. The addition of extra quaternary amino groups and the controlled use of sulphonic acid groups can lead to a range of dyes having overall positive charges ranging up to 6 or even more.

Cy3 (n=1) and Cy5 (n=2) and Cy7 (n=3) dyes have the added advantage of allowing multiplexing i.e. the use of mixtures of targets labelled with different dyes for simultaneous analysis. This concept can also be increased by varying the intermediate derivative between indole, thiazole and oxazole derivatives, and by altering the number of fused aromatic rings to the dye.

CHEMICAL STRATEGY

This section shows the chemistry envisaged in making cyanine dyes having positive charges from 2 to 6, most but not all of which fall within the scope of the claims. Each numbered paragraph starts with a general picture of a cyanine dye shown as a rectangle, having a single positive charge shown as + within a circle. To two corners of the rectangle are attached curved lines which may comprise at least one positive charge and/or at least one functional or reactive group Q or Q'; these curved lines correspond to $R^1$, $R^2$, $R^3$, $R^4$, $R^5$, $R^6$ and $R^7$, most usually $R^1$ and $R^2$, in the structures (1) and (2) shown above and in the claims. Some of the cyanine dyes have been made and are described below in the Examples; others are in preparation or are envisaged.

+2 DYES

1.

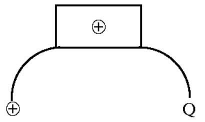

The dye carries an inherent +1 charge. A second + charge is located on a chain attached to one of the dye N atoms. A functional or reactive group Q terminates a chain attached to the other dye N atom.

EXAMPLES

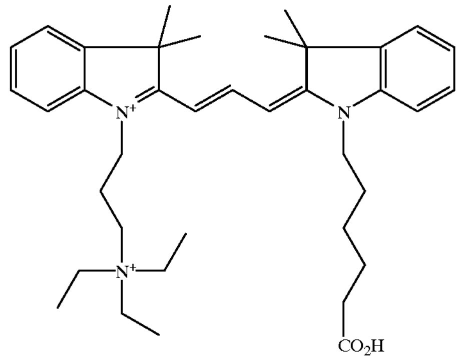

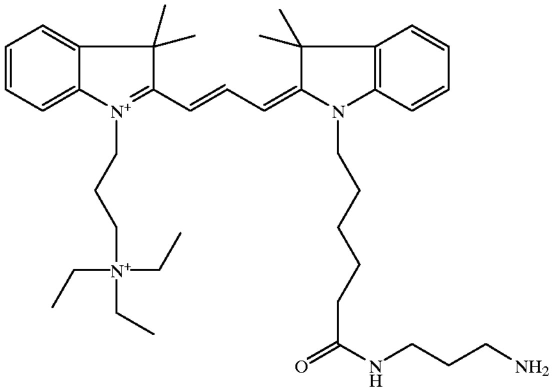

-continued

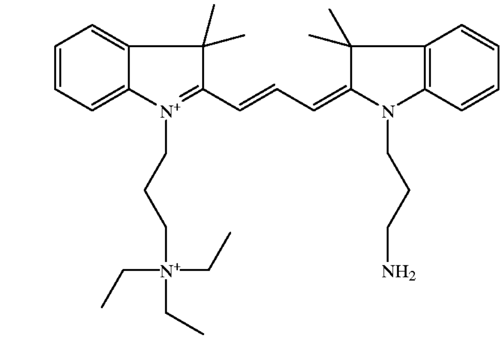

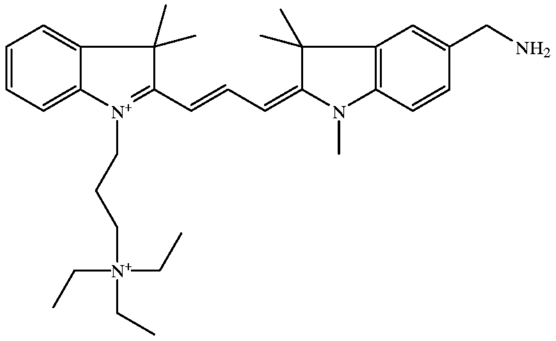

2.

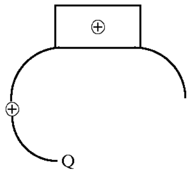

The dye carries an inherent +1 charge. A second + charge is located on a chain attached to one of the dye N atoms. A functional or reactive group Q terminates the same chain.

EXAMPLE

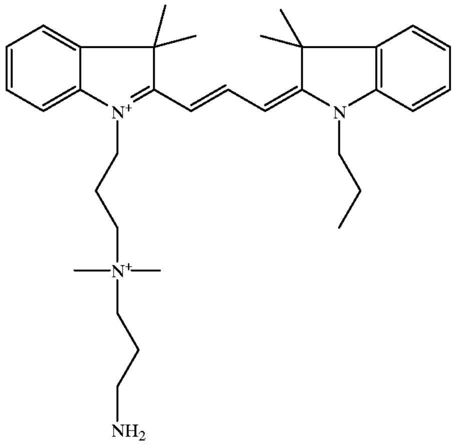

Synthesis of +2 intermediate:

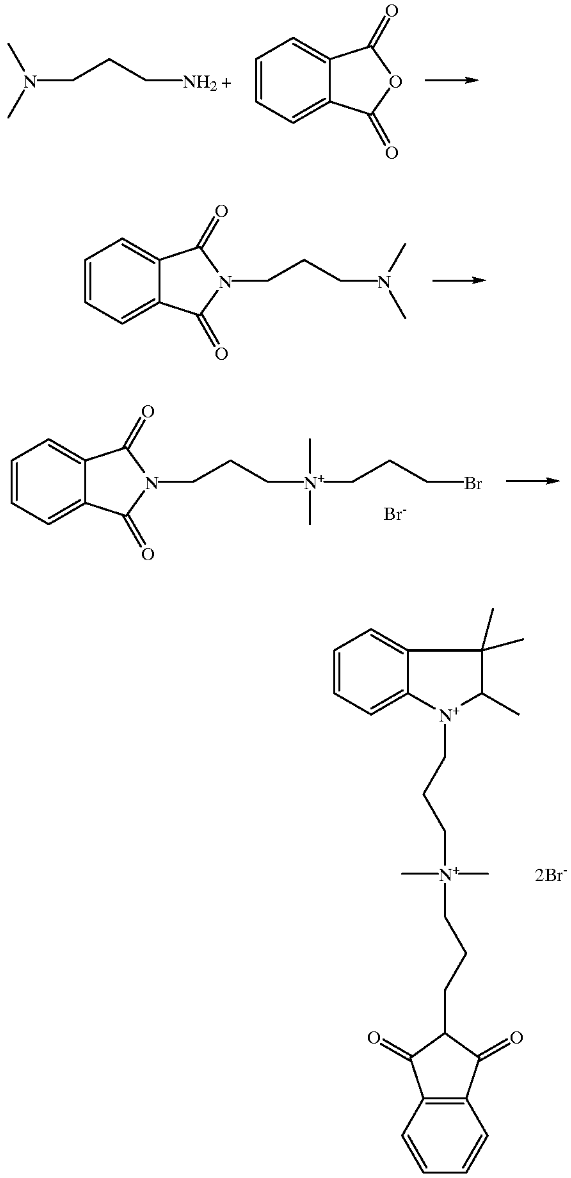

This intermediate is used to make the protected dye. The phthalimide is removed by hydrolysis in hydrochloric acid to give the amine dye.

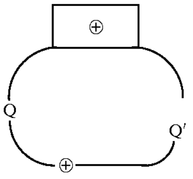

A +1 monoreactive dye is extended with a linker, which itself contains the second + charge. A possible example is as follows:

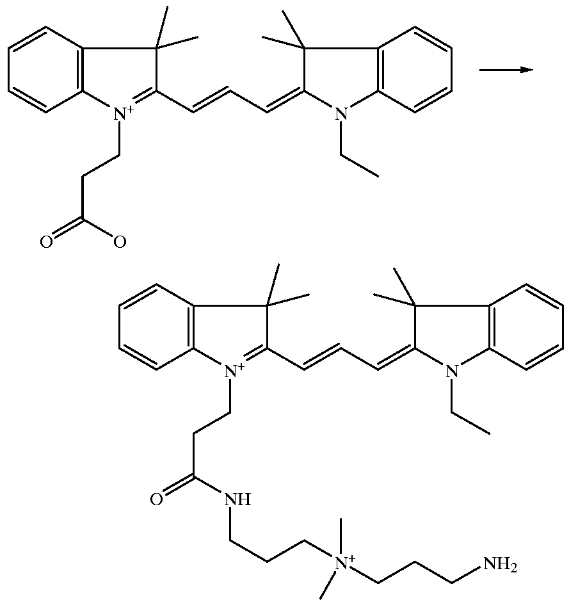

Projected synthesis of +1 linker:

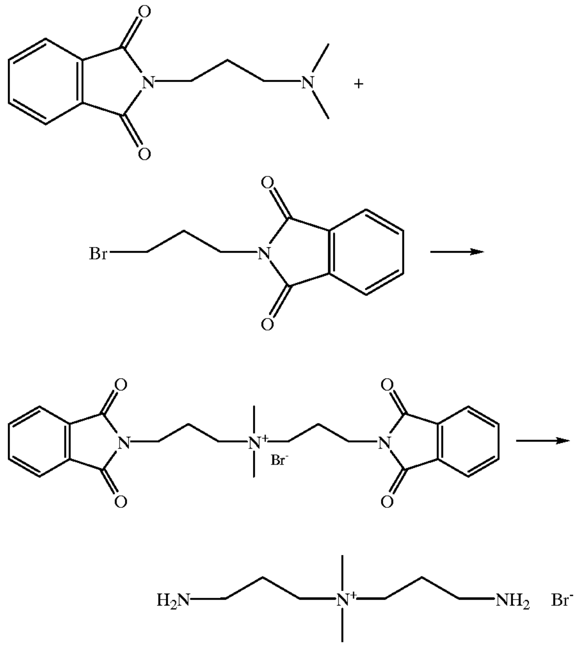

+3 DYES

These examples are analogous to those for +2 dyes.

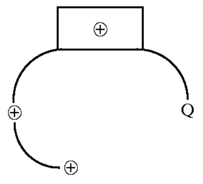

The dye carries an inherent +1 charge. The two extra + charges are located on a chain attached to one of the dye N atoms. A functional or reactive group Q terminates a chain attached to the other dye N atom.

EXAMPLES

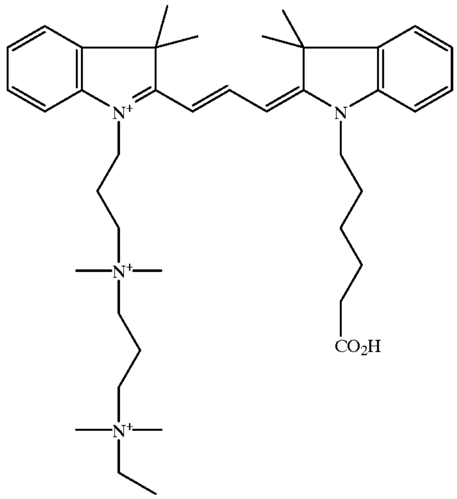

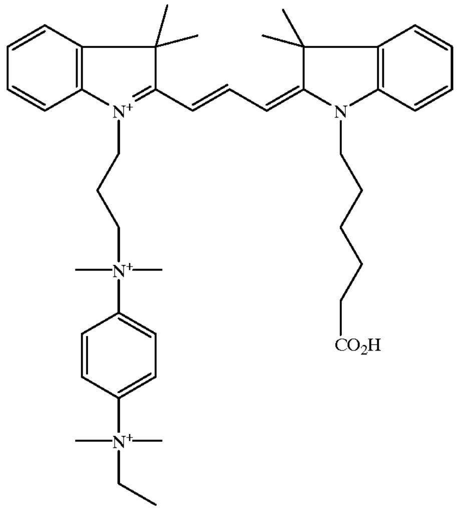

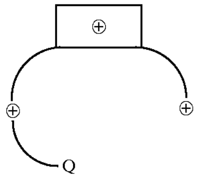

The dye carries an inherent +1 charge. There is one extra + charge on each chain attached to the dye N atoms. A functional or reactive group Q terminates one of these chains.

EXAMPLE
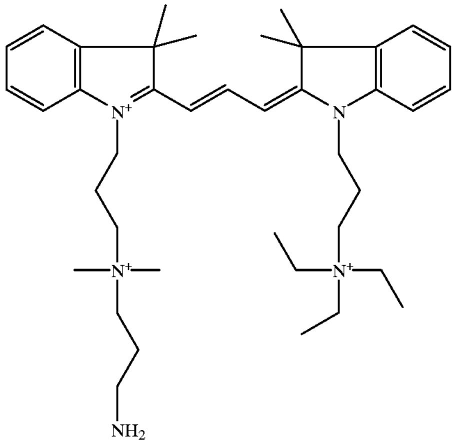
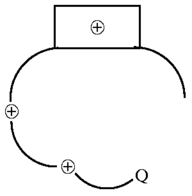
The dye carries an inherent + charge. The other two + charges are both on one chain off a dye N atom; this chain also includes a functional or reactive group Q. This requires a +3 charged intermediate containing a functional or reactive group.
EXAMPLES
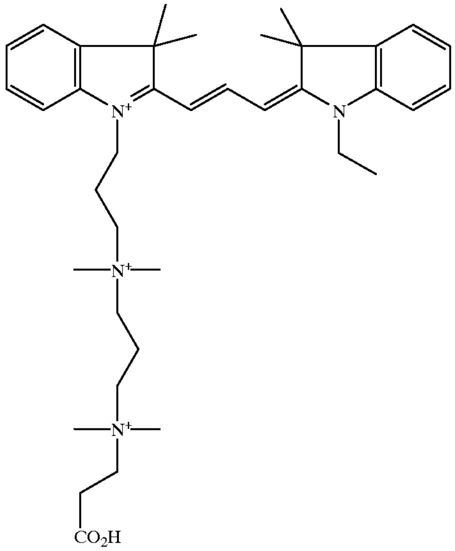
-continued
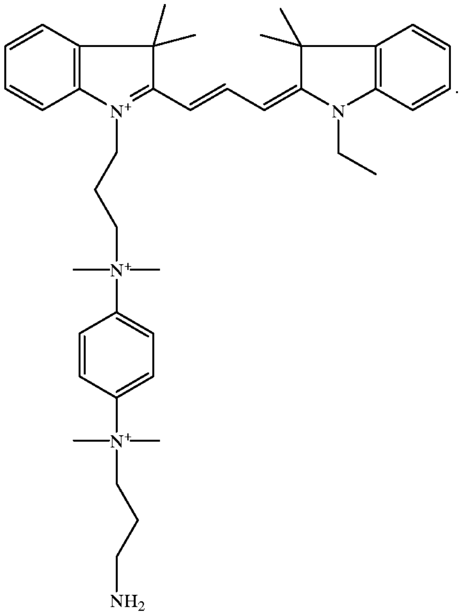
4. Conversion of a +2 dye to a +3 dye by addition of a +1 linker:
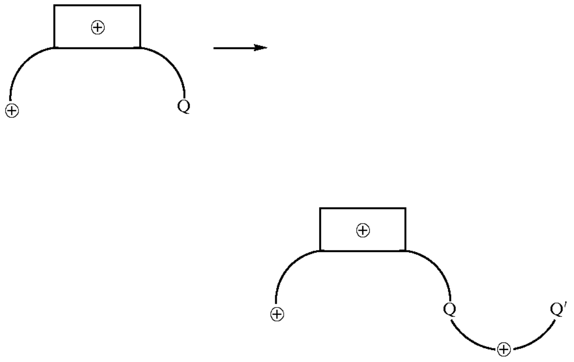
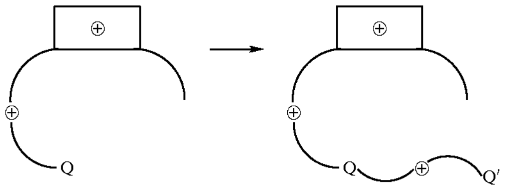

EXAMPLE
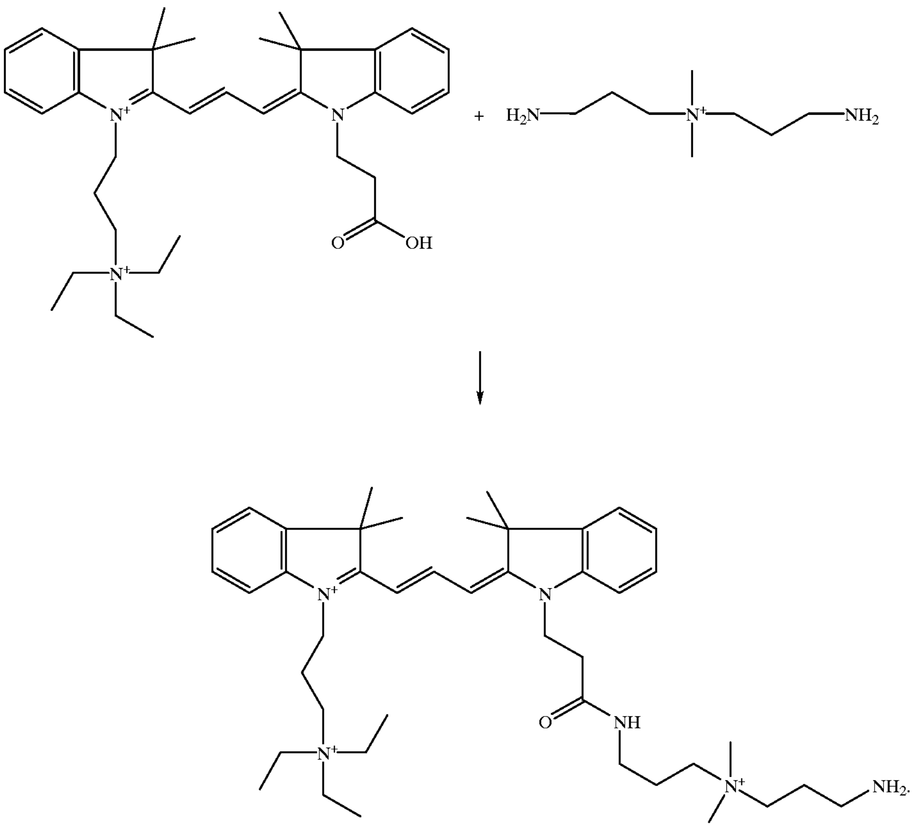
5. Conversion of a +1 dye to a +3 dye by addition of a +2 linker.
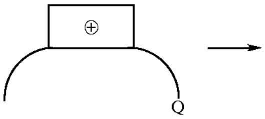
-continued
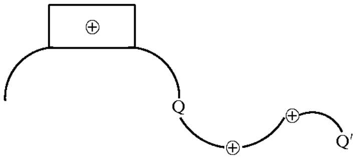
EXAMPLES
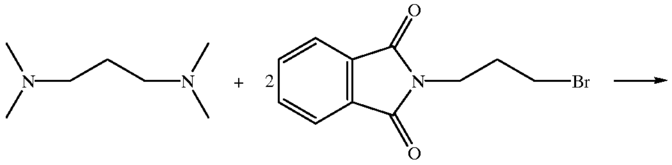
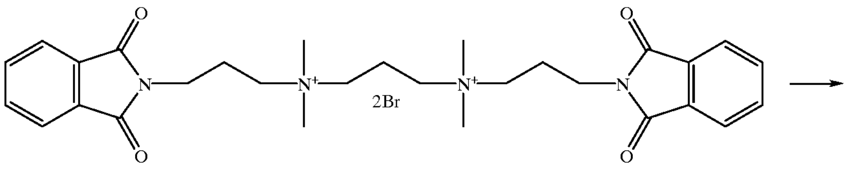

-continued
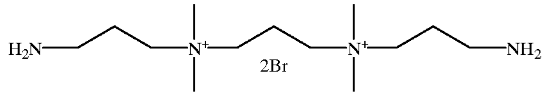
+3 dye:
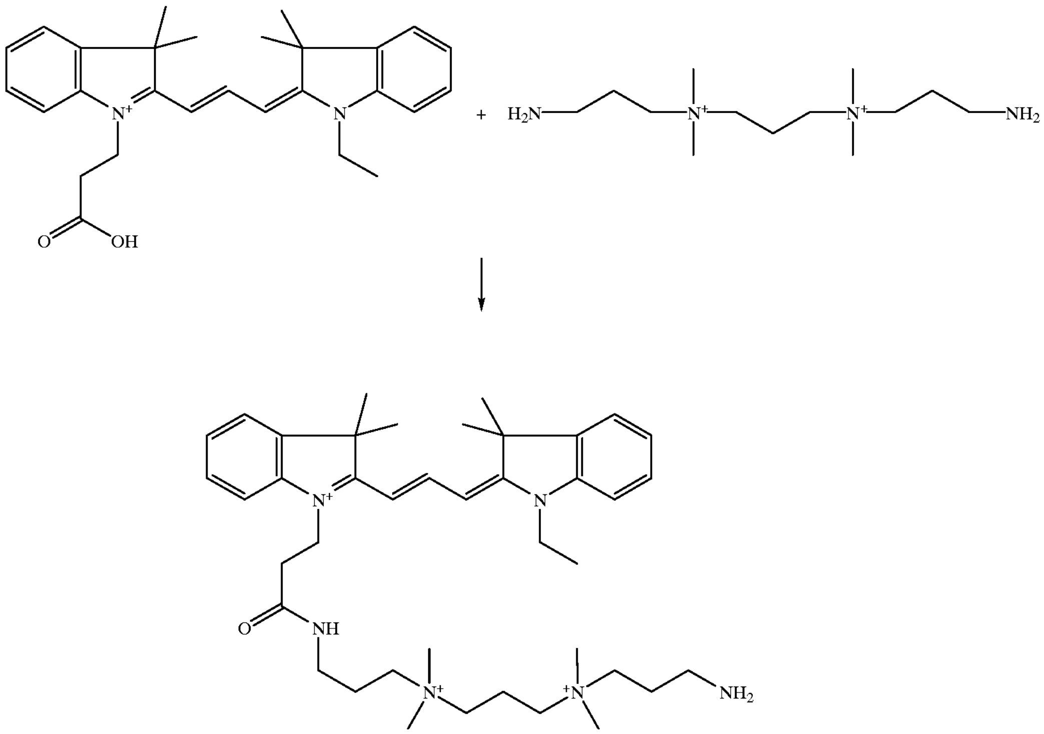
1. Conversion of a +2 dye to a +4 dye by addition of a +2 linker.
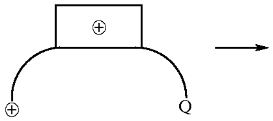
-continued
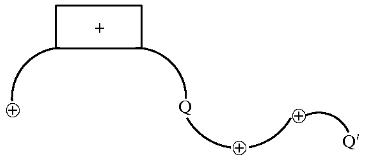
EXAMPLE
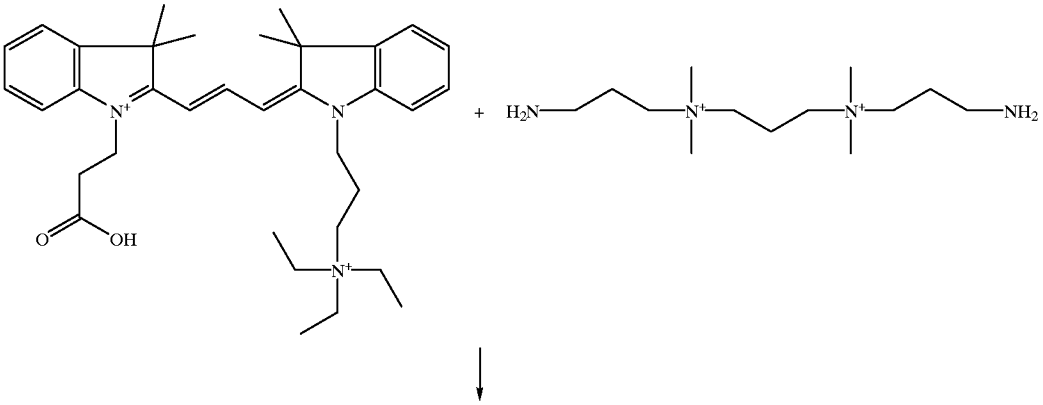

-continued
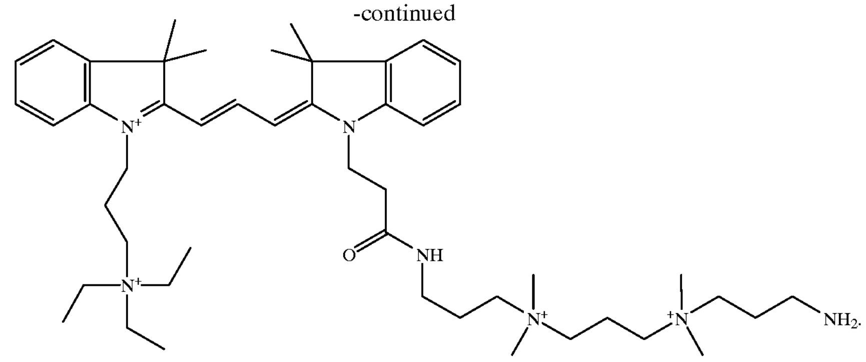
2. Conversion of a +1 dye to a +4 dye by addition of a +3 linker.
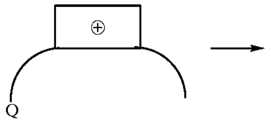
-continued
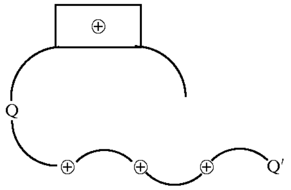
EXAMPLE
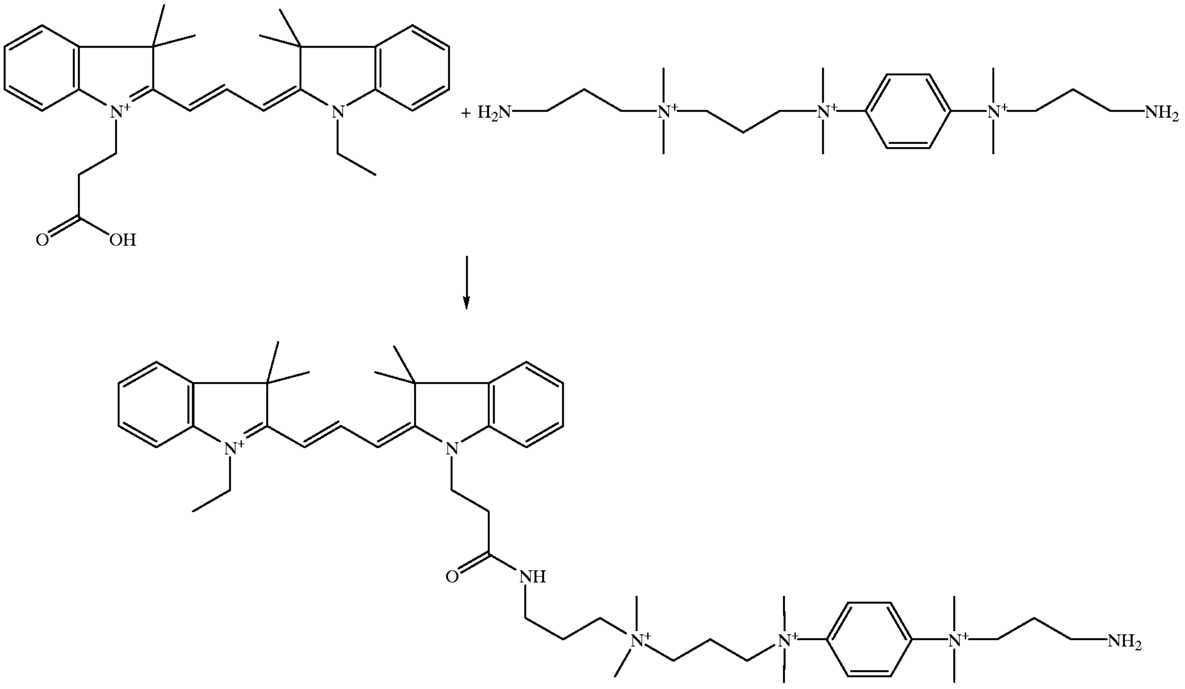
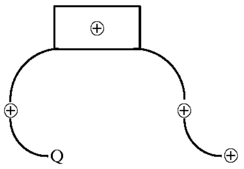

Requires a +2 intermediate with a reactive group and a +3 intermediate.
EXAMPLE
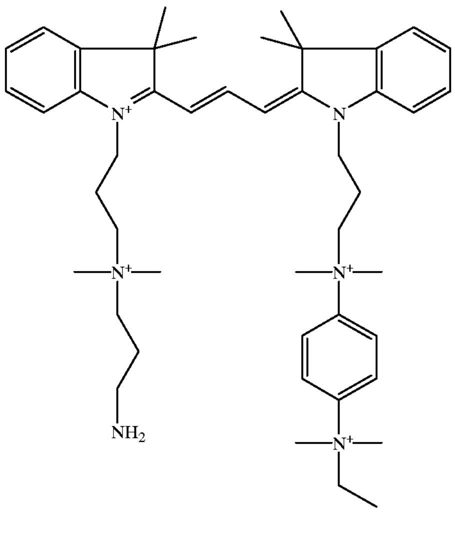
+5 and +6 DYES
1. Conversion of a +2 dye to a +5 dye by addition of a +3 linker:
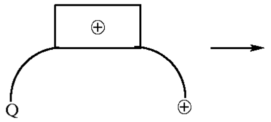
-continued
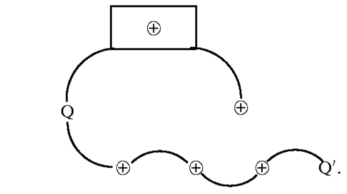
2. Conversion of a +1 dye to a +5 dye by addition of a +4 linker:
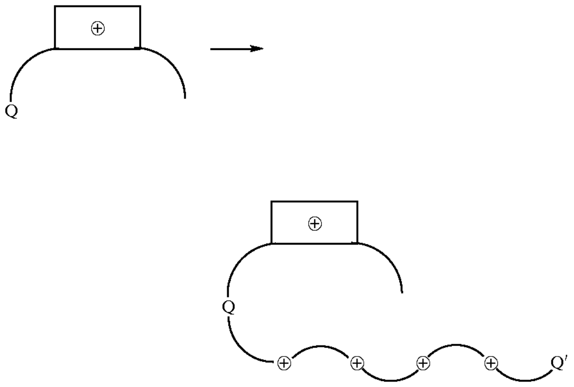
The +4 linker:
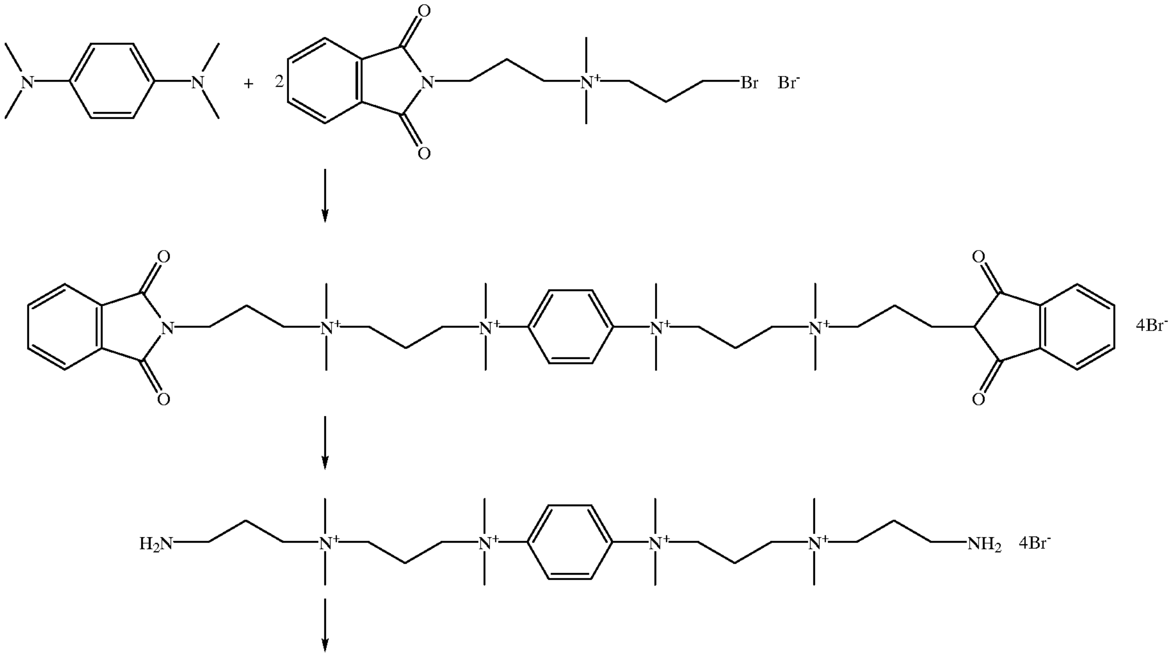

-continued
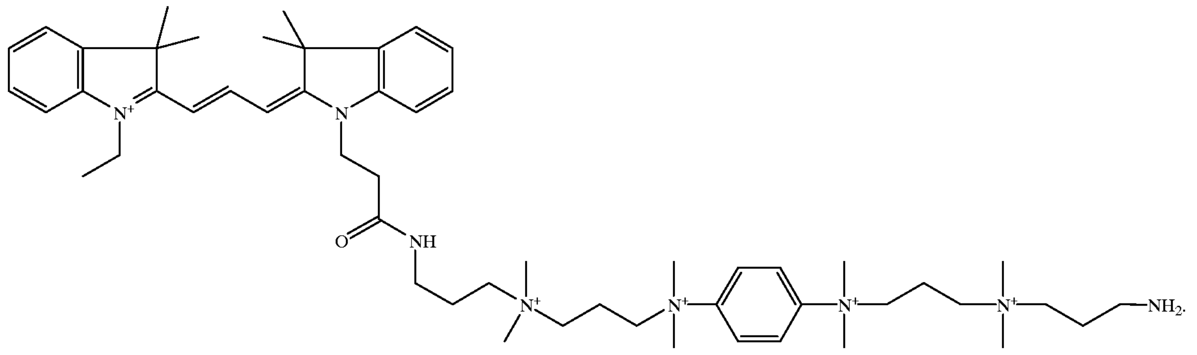
3. Conversion of a +2 dye to a +6 dye by addition of a +4 linker:
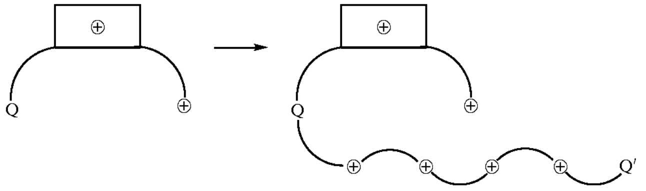
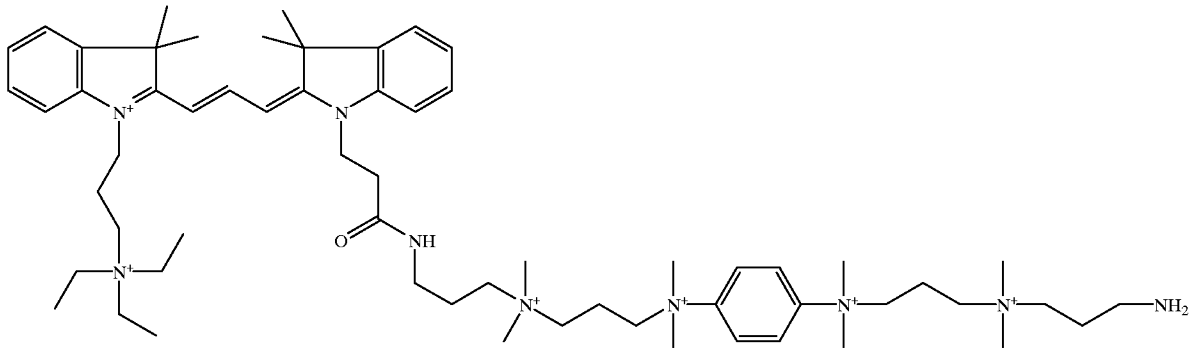
LINKER CHAINS BASED ON POLY-LYSINE
Lysine =
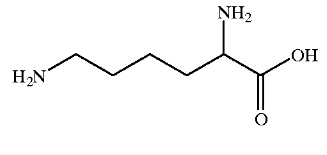
Also available:
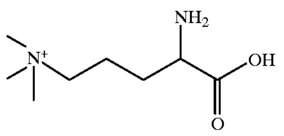
Construct oligomers on a solid support and couple to +1 dyes to give n+ dyes:
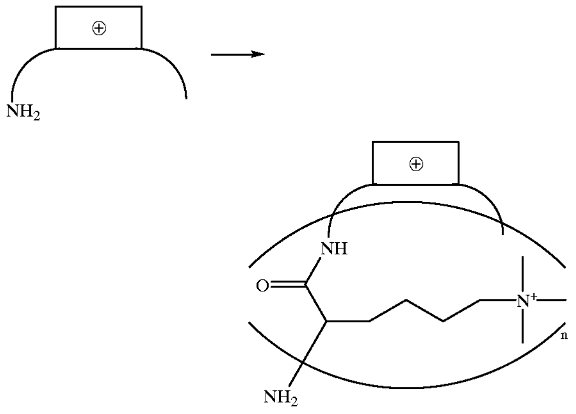
(n + 1) charged dye where n is 1–5 or 6

Example 1

+3 Charged dye, including +1 charged diamine linker (BOC-protected)

i) Preparation of a +2 charged carboxy Cy3 dye

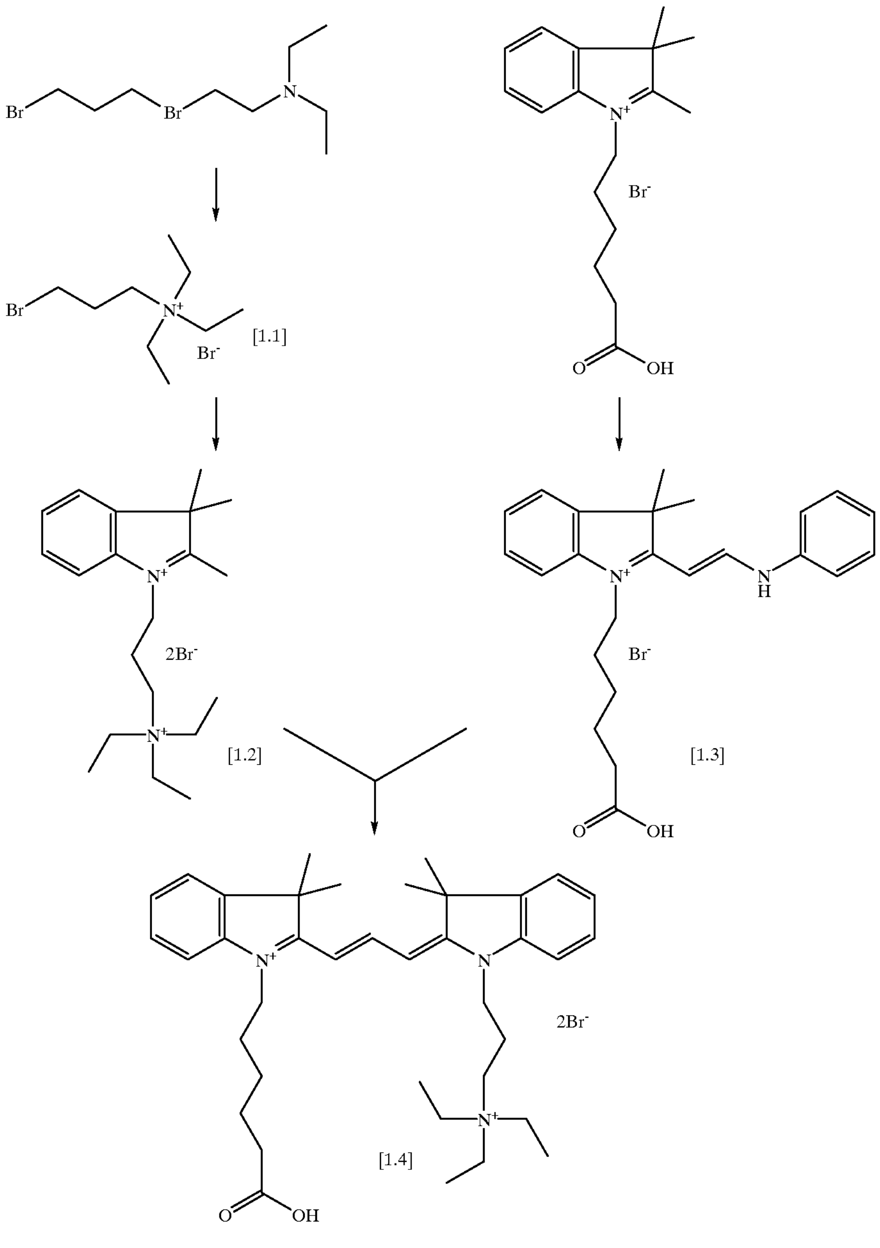

[1.1] [1.2] [1.3] [1.4]

1,3-Dibromopropane (20.0 g, 100 mmol) and triethylamine (5.06 g, 50 mmol) were mixed in dry toluene (50 ml). This solution was heated at 100° C. under nitrogen atmosphere for 4 hrs, during which time a thick white solid precipitated. The mixture was then cooled and the solid collected by filtration, washed with toluene and ether and dried under vacuum at 50° C. to give the title compound [1.1], 5.0 g (36%).

$\delta_H$ (300 MHz, DMSO) broad peaks. 1.17 (9H, 3× $N^+$—$CH_2$—$C\underline{H}_3$), 2.15 (2H, $BrCH_2C\underline{H}_2CH_2$—), 3.26 (8H, 4× $N^+$—$C\underline{H}_2$), 3.62 (2H, Br—$C\underline{H}_2$—).

1-((3-Triethylammonium)propyl)-2,3,3-trimethylindolium dibromide [1.2]

Freshly distilled 2,3,3-trimethylindolenine (0.8 g, 5 mmol) and N-(3-bromopropyl)triethylammonium bromide [1.1] (1.52 g, 5 mmol) were mixed and placed under an argon atmosphere. The mixture was then heated at 140° C. for 1.5 hrs, giving a deep red viscous melt, which solidified to a glass on cooling. It was ground to a powder under diethyl ether; this was collected by filtration, triturated with boiling acetone and recrystallised from methanol/acetonitrile to give the title compound [1.2] as a pale pink powder, 795 mg (34%).

$\delta_H$ (300 MHz, DMSO) 1.22 (9H, t, J 6.6 Hz, 3× $N^+$—$CH_2$—$C\underline{H}_3$), 1.55 (6H, s, indole $C3Me_2$), 2.21 (2H, m, —$CH_2C\underline{H}_2CH_2$—), 2.92 (3H, s, indole C2-Me), 3.27 (6H, q, J 6.6 Hz, 3× $N^+$—$C\underline{H}_2$—$CH_3$), 3.51 (2H, ~t, —$C\underline{H}_2$—$NEt_3$), 4.57 (2H, ~t, indole $N^+$—$C\underline{H}_2$—), 7.64 (2H, m), 7.86 (1H, d, J 6.5 Hz), 8.12 (1H, d, J 7.3 Hz).

1-(5-Carboxypentyl)-2-(N-phenyl-2-aminovinyl)-3,3-dimethylindolium bromide [1.3]

1-(5-carboxypentyl)-2,3,3-trimethylindolium bromide (1.77 g, 5 mmol) and N,N'-diphenylformamidine (1.96 g, 10 mmol) were mixed in acetic acid (15 m); the resulting mixture was then heated at reflux. The reaction was monitored by UV/VIS spectroscopy (methanol solution, product absorbance $\lambda_{max}$ 398 nm) and TLC (silica. Methanol, 20: dichloromethane, 80; product runs as a yellow streak, $R_f$ 0.1–0.25). After 2.5 hrs the orange-red solution was then left to cool over 16 hrs, then the solvent was removed under reduced pressure. The residue was purified by flash chromatography (silica. 5–20% methanol/dichloromethane) to give the title compound [1.3] as a yellow-orange foam after drying, 1.5 g (66%).

UV/VIS $\lambda_{max}$ (MeOH) 398 nm; $\delta_H$ (300 MHz, $CDCl_3$) 1.53 (2H, m), 1.63 (6H, s, indole C3 $Me_2$), 1.70 (2H, m), 1.78 (2H, m), 2.35 (2H, t, J 7.0 Hz, —$C\underline{H}_2$—$CO_2H$), 3.99 (2H, t, J 7.4 Hz, indole $N^+$—$C\underline{H}_2$—), 6.3 (2H, broad, $NH+CO_2H$), 7.0–7.45 (10H, m), 8.40 (2H, d, J 12.5).

1-(Carboxypentyl)-1'-((triethylammonium)propyl)-indocarbocyanine dibromide [1.4]

1-(5-Carboxypentyl)-2-(N-phenyl-2-aminovinyl)-3,3-dimethylindolium bromide [1.3] (229 mg, 0.5 mmol) was dissolved in anhydrous pyridine (5 ml) to give an orange solution. To this was added acetic anhydride (0.5 ml) and the mixture stirred for 5 mins. 1-((3-Triethylammonium) propyl)-2,3,3-trmethylindolium dibromide [1.2] (231 mg, 0.5 mmol) was then added and the mixture warmed briefly to aid dissolution of the solid. A deep red-pink colour soon formed.

After 2 hrs stirring the solvent was removed under reduced pressure and the residue dried under high vacuum. It was then purified by flash chromatography (grade I neutral alumina. 5–20% methanol/chloroform), isolating the major pink component, to give the title dye [1.4] as a red solid, 278 mg.

TLC (C-18 silica. Acetic acid, 50: water, 45: methanol, 5: $R_f$ pink spot 0.55). UV/VIS $\lambda_{max}$ (MeOH) 548 nm. Fluorescence (MeOH) $\lambda_{ex}$ 548 nm; $\lambda_{em}$ 564 nm. $\delta_H$ 300 MHz, $CD_3OD$) 1.17 (9H, t, J 6.5 Hz, 3× $N^+$—$CH_2C\underline{H}_3$), 1.32 (2H, m), 1.72–1.88 (16H,m), 2.2 (2H, t, J 7.3 Hz, —$C\underline{H}_2CO_2H$+2H, broad, $N^+$—$CH_2C\underline{H}_2CH_2NEt_3$), 3.37 (6H, q, J 6.5, 3× $N^+$—$C\underline{H}_2CH_3$), 3.50 (2H, m, —$C\underline{H}_2NEt_3$), 4.19+4.26 (2H, t, J 7.7 Hz, +2H, t, J 7.3 Hz, 2× indole $N^+$—$C\underline{H}_2$—), 4.59 (1H, broad, —$CO_2H$), 6.55 (1H, d, J 13.6 Hz, methine =CH—), 6.61 (1H, d, J 13.2 Hz, 2×methine=C$\underline{H}$-indole), 7.28–7.49 (6H, m), 7.54–58 (2H, m), 8.57 (1H, ~t, J~13.4 Hz, =CH—C$\underline{H}$=CH—).

ii) Preparation of a +1 charged diamine linker (BOC-protected)

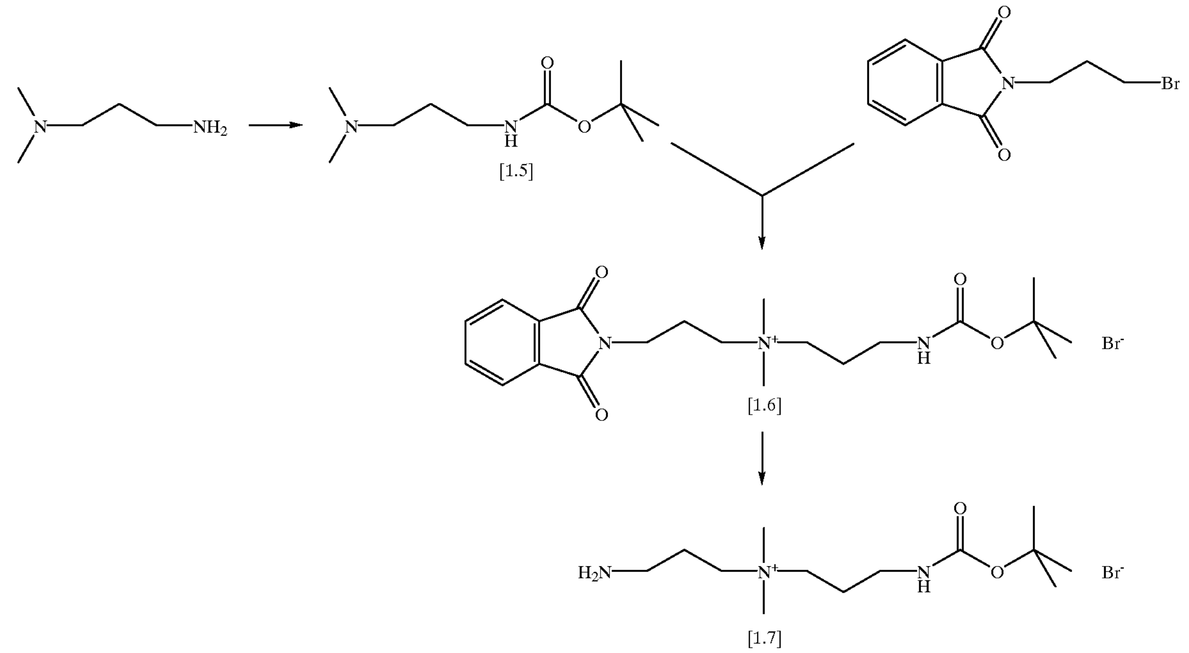

N-(t-Butoxycarbonyl)-N-(3-dimethylamino) propylamine [1.5]

3-Dimethylamino-1-propylamine (2.04 g, 20 mmol) was mixed with dichloromethane (5 ml); the resulting solution was cooled to 0° C. using an ice-water bath. To this was added a solution of di-t-butyl dicarbonate (4.4 g, 20 mmol) in dichloromethane (15 ml); the mixture was then allowed to warm to room temperature. After 2 hrs the solution was washed twice with water, then dried ($MgSO_4$), filtered and the solvent evaporated under reduced pressure to give a colourless oil. Drying under high vacuum gave the title compound, 3.07 g (76%).

$\delta_H$(300 MHz, $CDCl_3$) 1.44 (9H, s), 1.64 (2H, quin, J 6.8), 2.21 (6H, s), 2.31 (2H, t, J 7.0), 3.17 (2H, broad quartet) and 5.15 (1H, broad s).

N-(phthalimidopropyl)-N-((t-butoxycarbonylamino) propyl)-N,N-dimethylammonium bromide, [1.6]

N-(t-Butoxycarbonyl)-N-(3-dimethylamino)propylamine [1.5] (3.03 g, 15 mmol) and 3-(bromopropyl)phthalimide (4.02 g, 15 mmol) were dissolved in dry toluene (8 ml). The resulting solution was heated at 50° C. for 16 hrs, during which time a glassy resin formed on the inside of the flask. The mixture was cooled and the liquors decanted: the residue was triturated with ether to give a glassy powder. Dried under high vacuum to give the title compound [1.6], 4.12 g (58%).

$\delta_H$ (300 MHz, $CD_3OD$) 1.42 (9H, s), 1.91 (2H, m), 2.18 (2H, m), 3.07 (6H, s), 3.12 (2H, t, J 6.6), 3.3–3.5 (4H, m), 3.80 (2H, t, J 6.4) and 7.80–7.90 (4H, m).

N-(3-aminopropyl)-N-((t-butoxycarbonylamino) propyl)-N,N-dimethylammonium bromide, [1.7]

N-(phthalimidopropyl)-N-((t-butoxycarbonylamino) propyl)-N,N-dimethylammonium bromide [1.6] (4.1 g, 0.87 mmol) was dissolved in ethanolic methylamine (33 wt %, 8.02M, 10 ml). The colourless solution was stirred at room temperature for 3 days, during which time a thick white precipitate formed (N,N'-dimethylphthalamide). The mixture was filtered; the solid was washed with a little cold ethanol. The filtrate was evaporated under reduced pressure to give an oil; this was triturated with ether and dried under high vacuum to give the title compound [1.7] as a foam. Used without further purffication.

$\delta_H$ (300 MHz, $CD_3OD$) 1.43 (9H, s), 1.88–2.00 (4H, m), 2.75 (2H, t, J 6.8), 3.10 (6H, s), 3.15 (2H, t, J 6.6) and 3.3–3.5 (4H, m). A little N,N'-dimethylphthalamide also visible.

iii) Coupling of +2 charged Cy3 carboxy dye [1.4] to +1 charged linker [1.7]

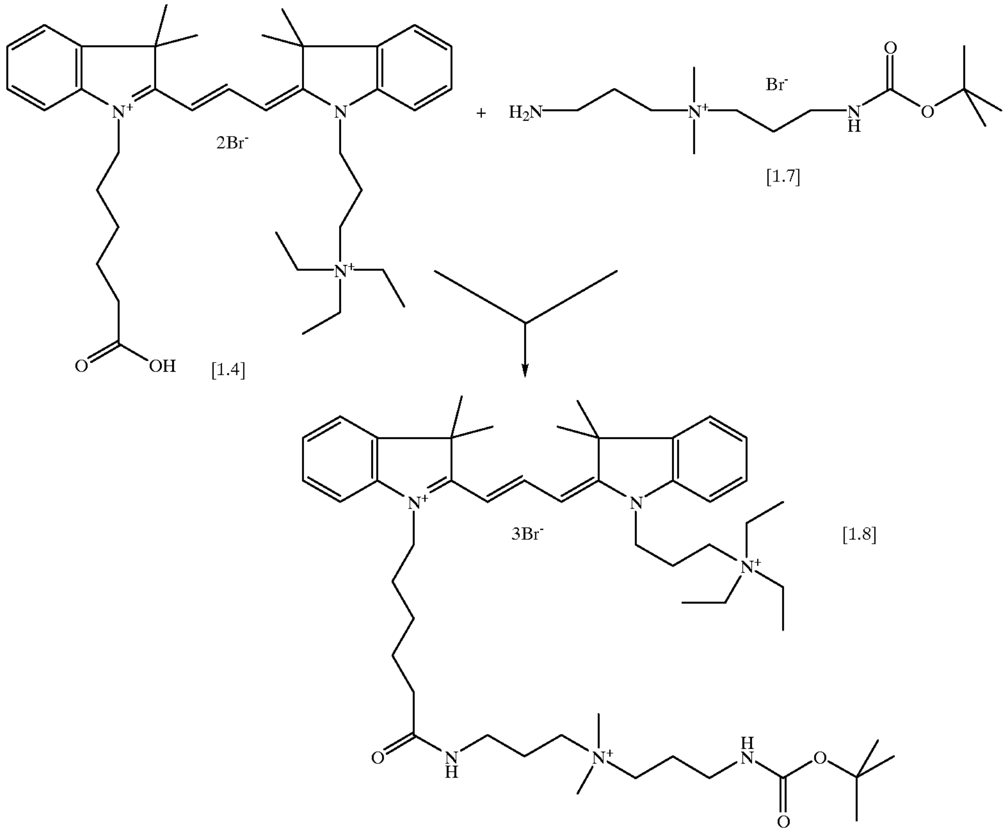

Dye [1.4] (37 mg, 50 $\mu$mol) and O—(N-succinimidyl)-N,N,N',N'-tetramethyluronium tetrafluoroborate (=TSTU, 17 mg, 55 $\mu$mol) were dissolved in dry acetonitrile (1 ml). To the resulting deep pink-red solution was then added N,N-diisopropylethylamine (10 $\mu$l, 57 $\mu$mol) and the mixture stirred at room temperature with TLC monitoring (silica. Methanol, 50: water, 50. Saturated with NaBr.Free acid [1.4], $R_f$=0.4→active ester, $R_f$=0.5). Once the activation was complete (1 hr), the amine [1.7] was added in portions, until TLC (as above) showed≈complete conversion (active ester $R_f$=0.5→[1.8] $R_f$=0.35). The solvent was then evaporated under reduced pressure; the residue was triturated with ether to give a brassy-coloured powder. Purified by preparative TLC, twice (silica, 20×20×0.1 cm with concentration zone. Methanol, 50: water, 50. Saturated with NaBr). The main pink band was scraped off and extracted with the eluant, then methanol. The solvent was removed under reduced pressure and the residue dried. Product dye was extracted from the NaBr using chloroform; again the solvent was removed under reduced pressure, to give the title compound [1.8], 24 mg.

UV/VIS $\lambda_{max}$ (MeOH); 548 nm $\delta_H$ (300 MHz, $CD_3OD$) 1.34 (9H, t, J 7.2), 1.41 (9H, s), 1.58 (2H, m), 1.67–2.03 (20H, m. Includes 2xs for gem-dimethyl groups), 2.25–2.31 (4H, m), 3.09 (6H, s), 3.13 (2H, t, J 6.3), 3.26 (2H, t, J 6.3), 3.3–3.5 (10H, m, partially obscured by $CHD_2OD$), 3.60 (2H, app. t), 4.24 (2H, broad t, J 7.6), 4.33 (2H, broad t, J 7.4), 6.90 (1H, d, J 13.6), 6.92 (1H, d, J 13.2), 7.28–7.58 (8H, m) and 8.58 (1H, t, J 13.4).

Deprotection to the free amine is achieved using trifluoroacetic acid in methanol I chloroform (see example 2 for details of the method).

Example 2

+3 Charged dye, including +2 charged diamine linker (BOC-protected)

i) Preparation of a +2 charged diamine linker (BOC-protected)

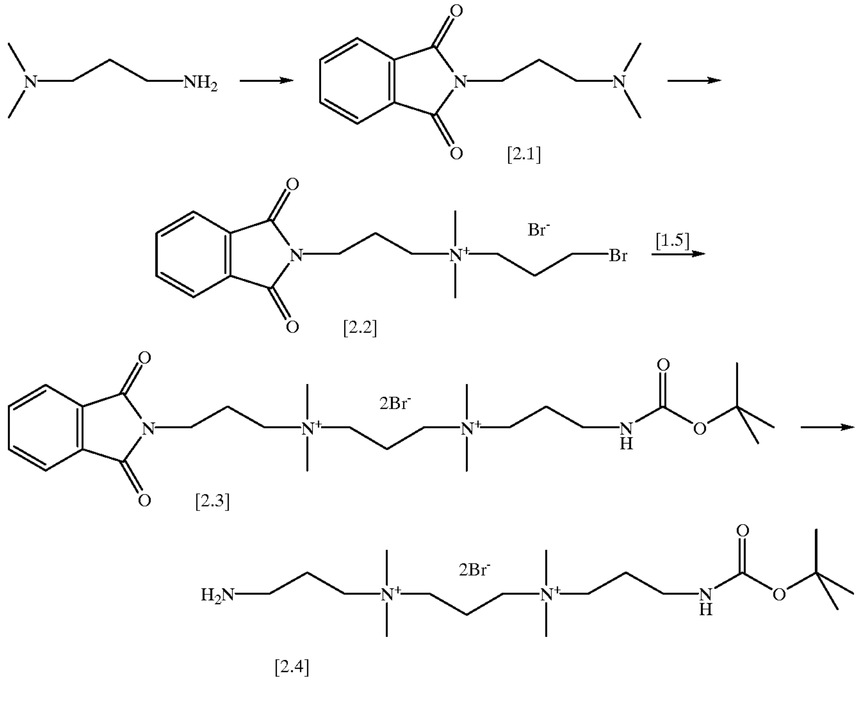

[2.1]
[2.2]
[2.3]
[2.4]

N-(3-Dimethylamino)phthalimide, [2.1]

3-Dimethylamine-1-propylamine (5.1 g, 50 mmol) and phthalic anhydride (8.15 g, 55 mmol) were mixed with chloroform (100 ml; the resulting mixture was heated under reflux for 4.5 hrs ($CaCl_2$ guard tube). After cooling the reaction mixture was washed twice with saturated aqueous sodium hydrogen carbonate solution, then with water. The organic solution was dried ($MgSO_4$), filtered and the solvent evaporated under reduced pressure to give a pale yellow oil. After drying under high vacuum, the title compound [2.1] was obtained, 10.2 g (88%).

$\delta_H$ (300 MHz, $CDCl_3$) 1.84 (2H, quin, J 7.2), 2.21 (6H, s), 2.34 (2H, t, J 7.3), 3.75 (2H, t, J 7.2), 7.70–7.74 (2H, m) and 7.82–7.86 (2H, m).

N-(3-Phthalimidopropyl)-N-(3-bromopropyl)-N,N-dimethylammonium bromide, [2.2]

N-(3-Dimethylamino)phthalimide [2.1] (2.32 g, 10 mmol) and 1,3-dibromopropane (4.04 g, 20 mmol) were dissolved in toluene (10 ml) to give a clear solution. This was warmed to 80° C. and stirred for 5 hrs. A white precipitate formed. After cooling, this solid was collected, washed with toluene and ether, and dried under vacuum to give the product, 3.55 g (82%).

$\delta_H$ (300 MHz, $D_2O$) 2.08 (2H, m), 2.20 (2H, m), 2.97 (6H, s), 3.27–3.40 (6H, m), 3.63 (2H, t, J 6.6) and 7.66–7.73 (4H, m).

N-(3-Phthalimidopropyl)-N'-(3-(t-butoxycarbonylamino)propyl)-N,N,N',N'-tetramethyl-1,3-propanediammonium dibromide, [2.3]

N-(3-Phthalimidopropyl)-N-(3-bromopropyl)-N,N-dimethylammonium bromide [2.2] (4.34 g, 10 mmol) and N-(t-Butoxycarbonyl)-N-(3-dimethylamino)propylamine [1.5] (2.02 g, 10 mmol) were mixed with acetonitrile (20 ml) and set stirring. The mixture was heated to 60° C., but not all solid dissolved. More acetonitrile was added in portions until an extra 20 ml had been added, whereupon all solids dissolved. This solution was allowed to react at 60° C. for 16 hrs. After this time the solution was cooled and the solvent evaporated under reduced pressure; the resinous foam that resulted was triturated with ether, then dried under high vacuum to give the title compound as a powder, 6.4 g (100%).

$\delta_H$ (300 MHz, $CD_3CN$) 0.86 (9H, s), 1.45 (2H, m, partly obscured by $CHD_2CN$), 1.66 (2H, m), 2.08 (2H, m), 2.58–2.70 (overlapping 6H, s+6H, s+2H, quartet), 2.86–3.06

(8H, m), 3.22 (2H, t, J 6.2), 5.70 (1H, broad app. t) and 7.23–7.32 (4H, m).

N-(3-Aminopropyl)-N'-(3-(t-butoxycarbonylamino) propyl)-N,N,N',N'-tetramethyl-1,3-propanediammonium dibromide, [2.4]

N-(3-Phthalimidopropyl)-N'-(3-(t-butoxycarbonylamino) propyl)-N,N,N',N'-tetramethyl-1,3-propanediammonium dibromide [2.3] (6.4 g, 10 mmol) was mixed with ethanolic methylamine (33 wt %, 8.02M, 10 ml) and set stirring. This was slow to all dissolve, so another 10 ml of reagent added; after a while all the resinous mass had dissolved. The mixture was then left to stir for 3 days at room temperature. During this time a white solid precipitated (N,N'-dimethylphthaiamide). This was removed by filtration and then rinsed through with a little cold ethanol. The filtrate was evaporated under reduced pressure; the residue was redissolved in ethanol and re-evaporated, twice. The final residue was triturated with ether and dried under high vacuum to give the title compound as a white solid (extremely deliquescent). This was stored under argon and used without further purification.

$\delta_H$ (300 MHz, $CD_3OD$) 1.34 (9H, s), 1.82–1.93 (4H, m), 2.28–2.39 (2H, m), 2.68 (2H, t, J 6.6), 3.02–3.18 (14H, m) and 3.42 (8H, app. quin.). A little N,N'-dimethylphthalamide also evident.

ii) Coupling of +1 charged Cy3 carboxy dye to +2 charged linker [2.4]

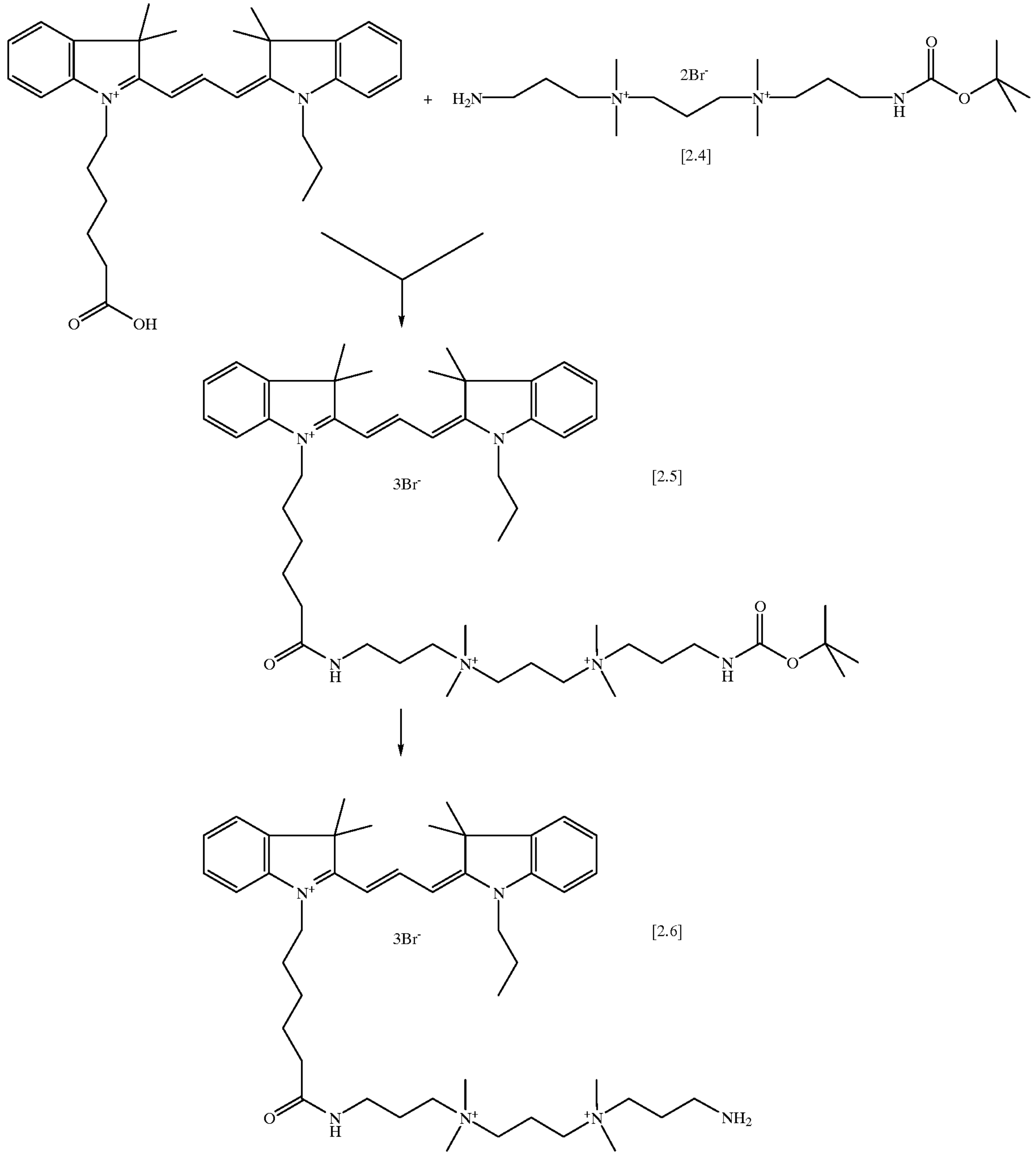

[2.4]

[2.5]

[2.6]

1-Propyl-1'-(carboxypentyl)indocarbocyanine dye (25 mg, ≈50 μmol) was dissolved in dry acetonitrile (2 ml), with stirring at room temperature. To the resulting pink-red solution was added O-(N-succinimidyl)-N,N,N',N'-tetramethyluronium tetrafluoroborate (=TSTU, 18 mg, 60 μmol) and N,N-diisopropylethylamine (5 μl, 60 μmol). Conversion to the active ester was monitored by TLC (silica. Methanol, 20: chloroform, 80. Carboxy dye, $R_f$=0.3→active ester $R_f$=0.5).

After 1 hr the amine [2.4] was added in portions, with TLC monitoring (silica. Methanol, 50: water, 50. Saturated with NaBr. Active ester $R_f$=0.55→[2.5] $R_f$=0.45). Once reaction was deemed to be complete the solvent was removed under reduced pressure, the residue triturated with ether and dried under high vacuum The crude product was purified by prep. TLC (silica, 20×20×0.2 cm with concentration zone. Methanol, 50: water, 50. Saturated with NaBr. Loaded in methanol solution). The main pink band was scraped off and extracted with the eluant, then methanol. The solvent was removed io under reduced pressure and the residue dried. Product dye was extracted from the NaBr using chloroform; again the solvent was removed under reduced pressure, to give the title compound [2.5], 30 mg. The compound was not characterised further but subjected to an amine deprotection. UV/VIS $\lambda_{max}$ (MeOH); 548 nm.

Deprotection of Amino Group to Give Free Amino Dye

Compound [2.5] (30 mg) was dissolved in 10% methanol/chloroform (2 ml); trifluoroacetic acid (0.5 ml) was then added and the mixture stirred at room temperature. Deprotection monitored by TLC (silica. Methanol, 50: water, 50. Saturated with NaBr. [2.5] $R_f$=0.55→[2.6] $R_f$=0.7). After 3 hrs the reaction was halted and the solvent removed under reduced pressure. The residue was triturated with ether and dried under high vacuum.

Purified by prep.TLC (silica, 20×20×0.2 cm with concentration zone. Methanol, 50: water, 50. Saturated with NaBr. Loaded in methanol solution). The main pink band was scraped off and extracted with the eluant, then methanol. The solvent was removed under reduced pressure and the residue dried. Product dye was separated from NaBr using a flash plug of activated charcoal. The crude dye was loaded in water and the plug eluted with water, methanol, then methanol, 1: chloroform, 1 to remove dye. The solvent was evaporated and the residue dried under high vacuum to give the title compound [2.6], 10 mg.

$\delta_H$ (300 MHz, $CD_3OD$, broadened peaks) 1.08 (3H, t, J 7.3), 1.52 (2H, m), 1.6–1.9 (20H, m), 2.02 (2H, m), 2.14–2.39 (6H, m), 3.09 (2H, app. t), 3.18–3.3 (14H, m), 3.45–3.65 (8H, broad m), 4.11–4.19 (4H, m), 6.51 (1H, d, J 13.2), 6.53 (1H, d, J 13.6), 7.28–7.56 (8H, m) and 8.55 (1H, t, J 13.4).

UV/VIS $\lambda_{max}$ (MeOH); 548 nm.

Example 3

+4 Charged dye, including +2 charged diamine linker (BOC-protected)

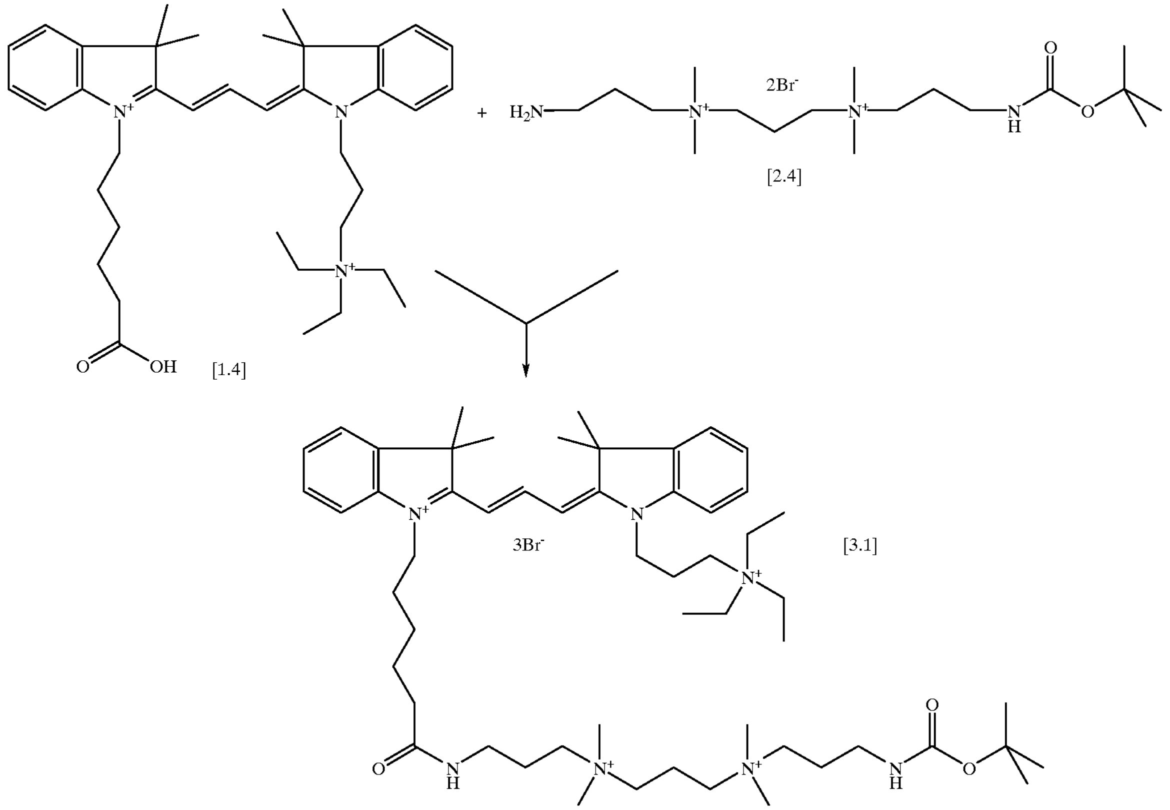

[1.4] [2.4] [3.1]

The +2 charged carboxy dye [1.4] (37 mg, ≈50 μmol) and O—(N-succinimidyl)-N,N,N',N'-tetramethyluronium tetrafluoroborate (TSTU, 17 mg, 55 μmol) were dissolved in dry acetonitrile (1 ml) to give a deep pink-red solution. To this was added N,N-diisopropylethylamine (10 μl, 57 μmol); the resulting solution was left to stir at room temperature. The reaction was monitored by TLC (silica. Methanol, 50: water, 50. Saturated with NaBr. [1.4] $R_f$=0.45→active ester, $R_f$=0.6).

After 1 hr the +2 amine linker, [2.4], was added portionwise with further TLC monitoring (as above. NHS ester, $R_f$=0.6→[3.1] $R_f$=0.4). Once the reaction appeared to be complete the solvent was evaporated under reduced pressure; the residue was left to stand under ether overnight. The ether was then decanted and the residue purified by prep. TLC (silica, 20×20×0.1 cm. Methanol, 50: water, 50. Saturated with to NaBr. Loaded in methanol solution). The main pink band was scraped off and extracted with the eluant, then methanol. The solvent was removed under reduced pressure and the residue dried. Product dye was extracted from the NaBr using chloroform; again the solvent was removed under reduced pressure, to give the title compound [3.1], 40 mg.

$\delta_H$ (300 MHz, $CD_3OD$) 1.34 (9H, t, J 7.2), 1.42 (9H, s), 1.57 (2H, app. quin.), 1.70–2.01 (20H, m), 2.19–2.36 (6H, m), 3.13–3.20 (6H, s+6H, s+2H, partly obscured), 3.3 (2H, m, partly obscured by $CHD_2OD$), 3.33–3.64 (16H, m), 6.87 (1H, d, J 13.6), 6.90 (1H, m, J 13.2), 7.28–7.59 (8H, m) and 8.58 (1H, t, J 13.4).

UV/VIS $\lambda_{max}$(MeOH); 548 nm.

Deprotection to the free amine is achieved using trifluoroacetic acid in methanol/chloroform (see example 2 for details of the method).

What is claimed is:

1. A cyanine dye having the structure (1)

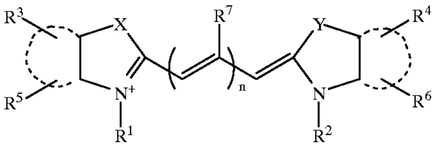

where the dotted lines represent the carbon atoms necessary for a one ring or a two or three fused ring system with 5 or 6 carbon atoms in each ring and $R^3$, $R^4$, $R^5$ and $R^6$ attached to the rings, X and Y are independently selected from O, S and $CR_2^8$, where $R^8$ is $C_1$–$C_4$ alkyl, n is 1, 2 or 3, at least one of $R^1$, $R^2$, $R^3$, $R^4$, $R^5$, $R^6$ and $R^7$ contains a reactive group that can react with a functional group of a target molecule or contains a functional group that can react with a reactive group of a target molecule, at least one of $R^1$, $R^2$, $R^3$, $R^4$, $R^5$, $R^6$ and $R^7$ contains one to five positively charged nitrogen or phosphorus or sulphur atoms, any remaining $R^3$, $R^4$, $R^5$ and $R^6$ is independently selected from H, $SO_3^-$, Cl, Br, $OR^9$ and $SR^9$, where $R^9$ is $C_1$–$C_{10}$ alkyl or aryl or aralkyl, any remaining $R^1$ and $R^2$ is independently selected from $C_1$–$C_{10}$ alkyl or aryl or aralkyl either unsubstituted or substituted by $SO_3$, any remaining $R^7$ is selected from H and $C_1$–$C_{10}$ alkyl or aryl or aralkyl either unsubstituted or substituted by $SO_3$, provided that at least two positively charged atoms selected from nitrogen and phosphorus and sulphur are present in the groups $R^1$, $R^2$, $R^3$, $R^4$, $R^5$, $R^6$ and $R^7$, and provided that the first atom of $R^7$ (through which it is linked to the rest of the molecule) is H or C.

2. A cyanine dye as claimed in claim 1, having an overall positive charge of +2 to +6.

3. A cyanine dye as claimed in claim 1, wherein a functional group, selected from primary amine, secondary amine, hydrazine, hydroxylamine, pyrazolone, sulphydryl, carboxyl, hydroxyl, thiophosphate, imidazole aldehyde and ketone, is present in at least one of $R^1$, $R^2$, $R^3$, $R^4$, $R^5$, $R^6$ and $R^7$.

4. A cyanine dye as claimed in claim 1, wherein a reactive group, selected from succinimidyl ester, isothiocyanate, dichlorotriazine, isocyanate, haloacetamide, maleimide, sulphonyl halide, acid halide, alkylimido ester, arylimido ester, carbodiimide, phosphoramidite, anhydride and acyl azide, is present in at least one of $R^1$, $R^2$, $R^3$, $R^4$, $R^5$, $R^6$ and $R^7$.

5. A cyanine dye as claimed in claim 1, wherein at least one of $R^1$, $R^2$, $R^3$, $R^4$, $R^5$, $R^6$ and $R^7$ is a branched or straight chain of up to 60 carbon atoms or comprises a chain of one or more amino acids.

6. A cyanine dye as claimed in claim 1, wherein the positively charged atoms are positively charged nitrogen atoms.

7. A cyanine dye as claimed in claim 5, wherein a branched or straight chain of up to 60 carbon atoms incorporating one to five positively charged nitrogen atoms has the structure $—(CH_2)_mN^+R^{10}R^{10}R^{11}$ or $—CH_2—Ph—N^+R^{10}R^{10}R^{11}$ where m is 1 to 4, $R^{10}$ is $C_1$–$C_{10}$ alkyl, and $R^{11}$ is $C_1$–$C_{10}$ alkyl or $—(CH_2)_mN^+R^{10}R^{10}R^{11}$.

8. A cyanine dye as claimed in claim 1, wherein at least one of $R^1$, $R^2$, $R^3$, $R^4$, $R^5$, $R^6$ and $R^7$ has the structure-L-Q where L is a linker and Q is the reactive or functional group.

9. A cyanine dye as claimed in claim 8, wherein the linker is a straight chain of 1–60 atoms selected from C, N, O, S and P.

10. A cyanine dye as claimed in claim 1 and having the structure (2)

(2)

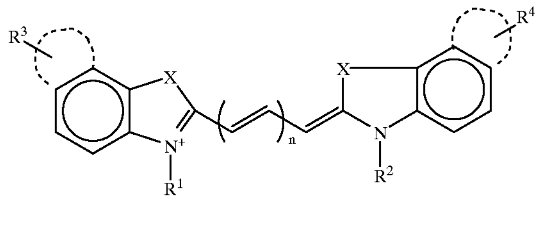

wherein X and Y are $C(CH_3)_2$ n is 1 or 2, $R^1$ is $—(CH_2)_5—COOH$, $R^2$ is $—(CH_2)_3—N^+(CH_3)_2—(CH_2)_3—N^+(CH_3)_2(C_2H_5)$, and $R^3$ and $R^4$ are H.

* * * * *